(12) United States Patent
Ratner et al.

(10) Patent No.: US 8,090,208 B2
(45) Date of Patent: Jan. 3, 2012

(54) ROBUST SEGMENTATION OF A MASS CANDIDATE IN DIGITAL MAMMOGRAPHY IMAGES

(75) Inventors: Eliahu Ratner, Jerusalem (IL); Philippe Nathan Bamberger, Jerusalem (IL)

(73) Assignee: Siemens Computer Aided Diagnosis Ltd., Jerusalem (IL)

( * ) Notice: Subject to any disclaimer, the term of this patent is extended or adjusted under 35 U.S.C. 154(b) by 1133 days.

(21) Appl. No.: 11/859,858

(22) Filed: Sep. 24, 2007

(65) Prior Publication Data

US 2008/0085057 A1   Apr. 10, 2008

Related U.S. Application Data

(60) Provisional application No. 60/849,014, filed on Oct. 4, 2006.

(51) Int. Cl.
*G06K 9/48* (2006.01)
(52) U.S. Cl. ....................................... 382/242
(58) Field of Classification Search .................. 382/242
See application file for complete search history.

(56) References Cited

U.S. PATENT DOCUMENTS

| | | | | |
|---|---|---|---|---|
| 2003/0099397 A1* | 5/2003 | Matsugu et al. | ............... | 382/173 |
| 2008/0137970 A1* | 6/2008 | Kubota | ............... | 382/224 |
| 2008/0187204 A1* | 8/2008 | Reeves et al. | ............... | 382/131 |

FOREIGN PATENT DOCUMENTS

| | | |
|---|---|---|
| WO | 2004/081874 A | 9/2004 |
| WO | 2005/114566 A | 12/2005 |
| WO | WO 2005114566 A2 * | 12/2005 |

OTHER PUBLICATIONS

Sheshadri et al., "Mammogram image analysis using recursive watershed algorithm", Proceedings of the Second lasted International Multi-Conference on Automation, Control and Information Technology, Jun. 2005, pp. 251-255.
Madabhushi et al., "Combining Low-, High-Level and Empircal Domain Ultrasonic Breast Lesions", IEEE Transactions on Medical Imaging, IEEE Service Center, Piscataway, NJ, vol. 22, No. 1, Feb. 1, 2003, pp. 155-169.
Timp et al., "A new 2D segmentation method based on dynamic programming applied to computer aided detection in mammography", Medical Physics, AIP, Melville, NY, vol. 31, No. 5, May 1, 2004, pp. 958-971.
Chu et al., "Graph-based region growing for mass-segmentation in digital mammography", Proceedings of the SPIE—The International Society for Optical Engineering, SPIE, Bellingham, VA, vol. 4684, Jan. 1, 2002, pp. 1690-1697.
International Search Report including Notification of Transmittal of the International Search Report, International Search Report, and Written Opinion of the International Searching Authority.

* cited by examiner

*Primary Examiner* — Brian Werner
*Assistant Examiner* — Nirav G Patel
(74) *Attorney, Agent, or Firm* — Peter Withstandley (57) ABSTRACT

An iterative method for segmentation of an object appearing in a digital image, where the object is defined by a difference in intensity from its immediate surrounding region. The method may also be used for segmenting tissue masses found in a digital image, including masses found in digital mammography.

23 Claims, 2 Drawing Sheets

ROBUST SEGMENTATION OF A MASS CANDIDATE IN DIGITAL MAMMOGRAPHY IMAGES

CROSS REFERENCE TO RELATED APPLICATION

The present application claims priority rights from U.S. Provisional Application 60/849,014, filed Oct. 4, 2006.

FIELD OF INVENTION

The present invention relates to the field of digital images, more specifically to a method for segmenting objects in digital images.

BACKGROUND OF THE INVENTION

In many circumstances, the segmentation of a mass candidate is based on an initial identification of a kernel area. However, identification of the initial kernel is often a non-robust process, that is, the exact definition of this kernel may be influenced by irrelevant factors. As a consequence, a non-robust segmentation of the mass candidate may be obtained, as can be illustrated by two examples.

In a Computer Aided Diagnosis (CAD) process, many mass candidates are usually generated. In order for the CAD process to attain a high sensitivity and specificity, the probability of malignancy for each mass candidate needs to be evaluated precisely. This is achieved using a large number of quantitative features that are extracted from the area of the candidate in the image. For ensuring the highest possible statistical significance of the extracted features, an accurate definition of the mass candidate area, that is mass segmentation, is needed.

The CAD mass candidate is often initially identified by some kernel area or by a rectangle or other closed contour approximately enclosing the candidate. The exact position of this identifier, i.e. the kernel or the enclosing contour, is influenced, inter alia by the positioning of the film mammogram in the feeder as well as by small variations in the brightness and contrast of the scanned image. It is also influenced by imaging conditions (KeV, mAs). In order for the overall CAD process to be robust, the mass candidate segmentation should not be influenced by such slight and insignificant variations in the image.

As an additional example of a non-robust segmentation of mass candidates, the following can be considered. A viewing station used for soft reading of mammography images may provide additional information on objects that are mass candidates selected by the radiologist. In such a context, the radiologist needs to select the object he wants to consider using a pointing device. This can be done, for example, by clicking within the object or by drawing a rectangle or any other circumscribing contour around the object. The naturally high variability of such object definition by the user produces a lack of robustness in the segmented object and, consequently, a lack of reliability in any additional information computed for the object.

The way the mass candidate is segmented depends greatly on what is seen as the 'center' of the mass. For example, a contour of the object may be constructed by analyzing the profile of grey levels using a gradient analysis along lines radiating from the 'center'. If the object's 'center' is moved, different radiating lines will be analyzed and a different contour will be obtained.

Due to the complexity of the internal structure of a mass candidate and to the large variability between candidates, it is at present difficult to define in an unequivocal manner an analytical method for the determination of the 'center' of the object.

SUMMARY OF THE INVENTION

The present invention provides a method for robust segmentation of a mass candidate through iterative determination of a preferred and robust object 'center'.

The method includes the following:

1. An initial object 'center' pixel—a seed pixel—is first selected either by a CAD system processor or by the user.
2. An initial object segmentation is performed based on the initial object 'center' pixel. Segmentation can be performed by any one of several known methods. These include:
   region growing methods
   dynamic programming methods where one of many possible contours is selected by minimizing a cost function.

Persons of the art will be aware that many region growing methods are known. Without intending to limit such methods, the region growing method set forth in Milan Sonka and J. Michael Fitzpatrick; "Graph-based region growing for mass-segmentation in digital mammography"; Proc. SPIE 4684, p. 1690-1697, Medical Imaging, 2002: Image Processing can be used in conjunction with the present invention.

Similarly persons of the art will be aware that many dynamic programming methods are known. Without intending to limit such methods, the dynamic processing method set forth in S. Timp and N. Karssemeijer, "A new 2D segmentation method based on dynamic programming applied to computer aided detection in mammography"; Medical Physics, May 2004; 31(5): 958-71 can be used in conjunction with the present invention.

These references are incorporated by referenced herein.

3. The geometrical center of the segmented object is calculated. This can be accomplished by anyone of several known methods such as the weighted center of gravity of several predetermined areas or an average x value and an average y value of all the x and y coordinates of the points on a contour path.
4. The new center is compared to the previous one and:
   i. If the new center is equivalent to the previous one, the process is stopped and the last object segmentation is accepted. The criterion for equivalence between object centers may be their full identity or a maximum defined distance between the new and previous centers or any other predefined criterion.
   ii. If the new center is not equivalent to the most immediate previous center but is equivalent to another previous center, the process is stopped and some other analysis is made to decide which of the previously computed segmentations will be accepted.
   iii. If the new center is not equivalent to any of the previous centers:
      a. If the number of iterations has reached a predefined number of iterations, the process is stopped and some other analysis is made to decide which of the previously computed segmentations will be selected.
      b. If the number of iterations has not reached a predefined number of iterations:
         a new object segmentation is established starting from the last calculated geometrical center, the new segmentation being effected using the method as above in 2; and then
         repeating steps #3 and #4.

The predefined number of iterations is an arbitrary parameter chosen to avoid endless looping within the method.

For the suboptimal case, the 'analysis' mentioned in (ii) and (iii.a) above is a method which compares all previously calculated object segmentations and then selecting one of them according to a predefined criterion. An example of one such criterion is the segmentation that is closest to the average of all of the segmentations.

It is an object of the present invention to provide a method for adding robustness when segmenting an object in a digital image from its background.

It is a further object of the present invention to provide a method for adding robustness when segmenting a mass object in a digital image from its background.

It is another object of the present invention to provide a method for adding robustness when segmenting a mass object in a digital image, where the mass object is a mass of living tissue, particularly mammalian tissue.

It is a further object to present an iterative method for determining a preferred and robust object segmentation associated with a center.

There is therefore provided in one aspect of the present invention a method for adding robustness when segmenting a mass object appearing in a digital image of mammalian tissue, the digital image provided by a medical image acquisition system and the method used with a computer aided diagnosis (CAD) system, said method comprising the following steps:

providing a reference object center pixel;

separating the mass object from its background in the digital image by determining a segmentation contour around the reference object center pixel and calculating an object center pixel within the segmentation contour;

comparing the calculated object center pixel to the reference object center pixel, and if they are deemed equivalent according to a predefined criterion, accepting the segmentation contour from which the calculated object center pixel was determined; and     if the calculated and reference object center pixels are deemed to be non-equivalent, iterating said steps of providing, separating and comparing until equivalence is reached or until a predefined number of iterations is reached, which ever is first, and     wherein the reference object center pixel in the initial cycle of said method is a user or CAD system selected pixel, and in all said steps of iterating of said method, the reference object center pixel is the immediate previously calculated object center pixel.

In another embodiment of the present invention the method further includes, prior to the step of iterating, a second step of comparing wherein the reference object center pixel is compared to previously calculated object center pixels and if no equivalence is found effecting said step of iterating, and if equivalence is found, said method further includes a step of applying other analysis to select one of the previously determined segmentation contours. In this embodiment the analysis in the step of applying other analysis is selected from a group consisting of the following types of analyses:

a. choosing the previously calculated object center pixel that is closest to the average position of the previously calculated object center pixels and selecting the corresponding segmentation contour for the object;

b. calculating the average position of the previously calculated object center pixels and determining thereof a segmentation contour for the object;

c. sorting the previously determined segmentation contours for the mass object according to their enclosed surface and selecting the segmentation contour corresponding to the median surface; and     d. calculating the average surface of the previously determined segmentation contours for the object and selecting the segmentation contour whose surface is closest to the average surface.

In another embodiment of the method of the present invention, if equivalence is not reached before the predefined number of iterations is reached, said method further includes a step of applying other analysis to select one of the previously determined segmentation contours. In this embodiment the analysis in the step of applying other analysis is selected from a group consisting of the following types of analyses:

a. choosing the previously calculated object center pixel that is closest to the average position of the previously calculated object center pixels and selecting the corresponding segmentation contour for the object;

b. calculating the average position of the previously calculated object center pixels and determining thereof a segmentation contour for the object;

c. sorting the previously determined segmentation contours for the mass object according to their enclosed surface and selecting the segmentation contour corresponding to the median surface; and     d. calculating the average surface of the previously determined segmentation contours for the object and selecting the segmentation contour whose surface is closest to the average surface.

In another embodiment of the method of the present invention, the criterion for equivalence is selected from a group consisting of the following criteria: a. full spatial coordinate identity of the calculated and reference object center pixels; b. a maximum defined distance between the calculated and reference object center pixels; c. a minimum percentage of the area enclosed by the contour corresponding to the calculated object center pixel overlapping the area enclosed by the contour corresponding to the reference object center pixel.

In yet another embodiment of the method the segmentation contour in said step of separating is determined by using a method selected from a group consisting of the following methods:

region growing and dynamic programming where one of many possible contours is selected by minimizing a cost function.

In still another embodiment of the method where in said step of separating, calculating the object center pixel within the segmented mass object is effected by using a method selected from a group consisting of one of the following methods: a. computing the center of gravity of the area enclosed within the segmented contour; b. averaging separately the x and y coordinates of all the pixels located on the segmented contour; and c. computing separately the root mean square of the x and y coordinates of all the pixels located on the segmented contour.

In yet another aspect of the present invention there is provided a method for adding robustness when segmenting a mass object appearing in a digital image of mammalian tissue, the digital image provided by a medical image acquisition system and the method used with a computer aided diagnosis (CAD) system, said method comprising the following steps:

choosing a reference object center pixel of the mass object in the digital image;

separating the mass object from its background by determining an initial segmentation contour for the object around the reference object center pixel and calculating an object center pixel within the segmentation contour;

comparing the calculated object center pixel to the reference object center pixel;

accepting the segmentation contour if the calculated object center pixel is deemed equivalent to the reference object center pixel in said step of comparing;

if the calculated object center pixel is not deemed to be equivalent to the reference object center pixel in said step of comparing, executing a second step of comparing where the last calculated object center pixel is compared to previously calculated object center pixels; and where if the last calculated object center pixel is deemed equivalent to a previously calculated object center pixel in said second step of comparing, said method includes a step of further analysis, whereby one of the previously determined segmentation contours is accepted; and where if the last calculated object center pixel is not deemed equivalent to a previously calculated object center pixel in said second step of comparing, repeating said steps of choosing, separating, comparing, accepting and said second step of comparing, and wherein the reference object center pixel in the initial cycle of said method is a user or CAD system selected pixel, and in all said steps of repeating of said method it is the immediate previously calculated object center pixel.

In an embodiment of the method the analysis in the step of further analysis is selected from a group consisting of the following types of analysis:

a. choosing the previously calculated object center pixel that is closest to the average position of the previously calculated object center pixels and selecting the corresponding segmentation contour for the object;

b. calculating the average position of the previously calculated object center pixels and determining thereof a segmentation contour for the object;

c. sorting the previously determined segmentation contours for the mass object according to their enclosed surface and selecting the segmentation contour corresponding to the median surface; and d. calculating the average surface of the previously determined segmentation contours for the object and selecting the segmentation contour whose surface is closest to the average surface.

In yet another embodiment of the method of the present invention, said step of repeating is performed when the number of previous iteration cycles is less than a predefined number of iteration cycles.

In yet another embodiment of the method when the number of segmenting iterations is equal to a predefined number of iteration cycles, said method includes a step of further analysis whereby one of the previously determined segmentation contours is accepted. In this embodiment the analysis in the step of further analysis is selected from a group consisting of the following types of analysis:

a. choosing the previously calculated object center pixel that is closest to the average position of the previously calculated object center pixels and selecting the corresponding segmentation contour for the object;

b. calculating the average position of the previously calculated object center pixels and determining thereof a segmentation contour for the object;

c. sorting the previously determined segmentation contours for the mass object according to their enclosed surface and selecting the segmentation contour corresponding to the median surface; and d. calculating the average surface of the previously determined segmentation contours for the object and selecting the segmentation contour whose surface is closest to the average surface.

In still another embodiment of the method the criterion for equivalence is selected from a group consisting of the following criteria: a. full spatial coordinate identity of the calculated and reference chosen object center pixels; b. a maximum defined distance between the calculated and reference object center pixels; c. a minimum percentage of the area enclosed by the contour corresponding to the calculated object center pixel overlapping the area enclosed by the contour corresponding to the reference object center pixel.

In yet another embodiment of the method in said step of separating, calculating the object center pixel within the segmented mass object is effected by using a method selected from a group consisting of the following methods: a. computing the center of gravity of the area enclosed within the segmented contour; b. averaging separately the x and y coordinates of all the pixels located on the segmented contour; and c. computing separately the root mean square of the x and y coordinates of all the pixels located on the segmented contour.

In another embodiment of the method the segmentation contour in said step of separating is effected using a method selected from a group consisting of the following methods:
region growing and
dynamic programming where one of many possible contours is selected by minimizing a cost function.

In another aspect of the present invention there is provided a method for adding robustness when segmenting an object appearing in a digital image, where the object is defined by a difference in intensity from its immediate surrounding region and the digital image is provided by a computer system, said method comprising the following steps:

providing a reference object center pixel;

separating the object from its background in the digital image by determining a segmentation contour for the object around the reference object center pixel and calculating an object center pixel within the segmentation contour;

comparing the calculated object center pixel to the reference object center pixel, and if they are deemed equivalent according to a predefined criterion, accepting the segmentation contour from which the calculated object center pixel was determined; and if the calculated and reference object center pixels are deemed to be non-equivalent, iterating said steps of providing, separating and comparing until equivalence is reached or until a predefined number of iterations is reached, which ever is first, wherein the reference object center pixel in the initial cycle of said method is a user or CAD system selected pixel, and in all said steps of iterating, the reference object center pixel is the immediate previously calculated object center pixel.

In an embodiment of the third method provided by the present invention, the method further includes, prior to the step of iterating, a second step of comparing wherein the reference object center pixel is compared to previously calculated object center pixels and if no equivalence is found effecting said step of iterating, and if equivalence is found, said method further includes a step of applying other analysis to select one of the previously determined segmentation contours. In this embodiment the analysis in the step of applying other analysis is selected from a group consisting of the following types of analyses:

a. choosing the previously calculated object center pixel that is closest to the average position of the previously calculated object center pixels and selecting the corresponding segmentation contour for the object;
b. calculating the average position of the previously calculated object center pixels and determining thereof a segmentation contour for the object;
c. sorting the previously determined segmentation contours for the object according to their enclosed surface and selecting the segmentation contour corresponding to the median surface; and
d. calculating the average surface of the previously determined segmentation contours for the object and selecting the segmentation contour whose surface is closest to the average surface.

In yet another embodiment of the third method of the present invention where if equivalence is not reached before the predefined number of iterations is reached, said method further includes a step of applying other analysis to select one of the previously determined segmentation contours. In this embodiment, the analysis in the step of applying other analysis is selected from a group consisting of the following types of analyses:
a. choosing the previously calculated object center pixel that is closest to the average position of the previously calculated object center pixels and selecting the corresponding segmentation contour for the object;
b. calculating the average position of the previously calculated object center pixels and determining thereof a segmentation contour for the object;
c. sorting the previously determined segmentation contours for the object according to their enclosed surface and selecting the segmentation contour corresponding to the median surface; and
d. calculating the average surface of the previously determined segmentation contours for the object and selecting the segmentation contour whose surface is closest to the average surface.

In yet another embodiment of the third method of the present invention the criterion for equivalence is selected from a group consisting of the following criteria: a. full spatial coordinate identity of the calculated and reference object center pixels; b. a maximum defined distance between the calculated and reference object center pixels; c. a minimum percentage of the area enclosed by the contour corresponding to the calculated object center pixel overlapping the area enclosed by the contour corresponding to the reference object center pixel.

In a further embodiment of the third method of the present invention the segmentation contour in said step of separating is determined by using a method selected from a group consisting of the following methods:
region growing and
dynamic programming where one of many possible contours is selected by minimizing a cost function.

In still another embodiment of the third method of the present invention, in said step of separating, calculating the object center pixel within the segmented object is effected by using a method selected from a group consisting of one of the following methods: a. computing the center of gravity of the area enclosed within the segmented contour; b. averaging separately the x and y coordinates of all the pixels located on the segmented contour; and c. computing separately the root mean square of the x and y coordinates of all the pixels located on the segmented contour.

BRIEF DESCRIPTION OF THE FIGURES

The invention is herein described, by way of example only, with reference to the accompanying Figures. With specific reference now to the Figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show details of the invention in greater detail than is necessary for a fundamental understanding of the invention, the description taken with the Figures making apparent to those skilled in the art how the several forms of the invention may be embodied in practice.

The present invention will be more fully understood and its features and advantages will become apparent to those skilled in the art by reference to the ensuing description, taken in conjunction with the accompanying Figures, in which.

DETAILED DESCRIPTION OF THE PREFERRED EMBODIMENTS OF THE INVENTION

The present invention describes a method for the robust segmenting of a mass candidate in a digital medical image through iterative determination of the mass's center. The method may be applied to the segmenting of any object in any digital image.

Figure 1:
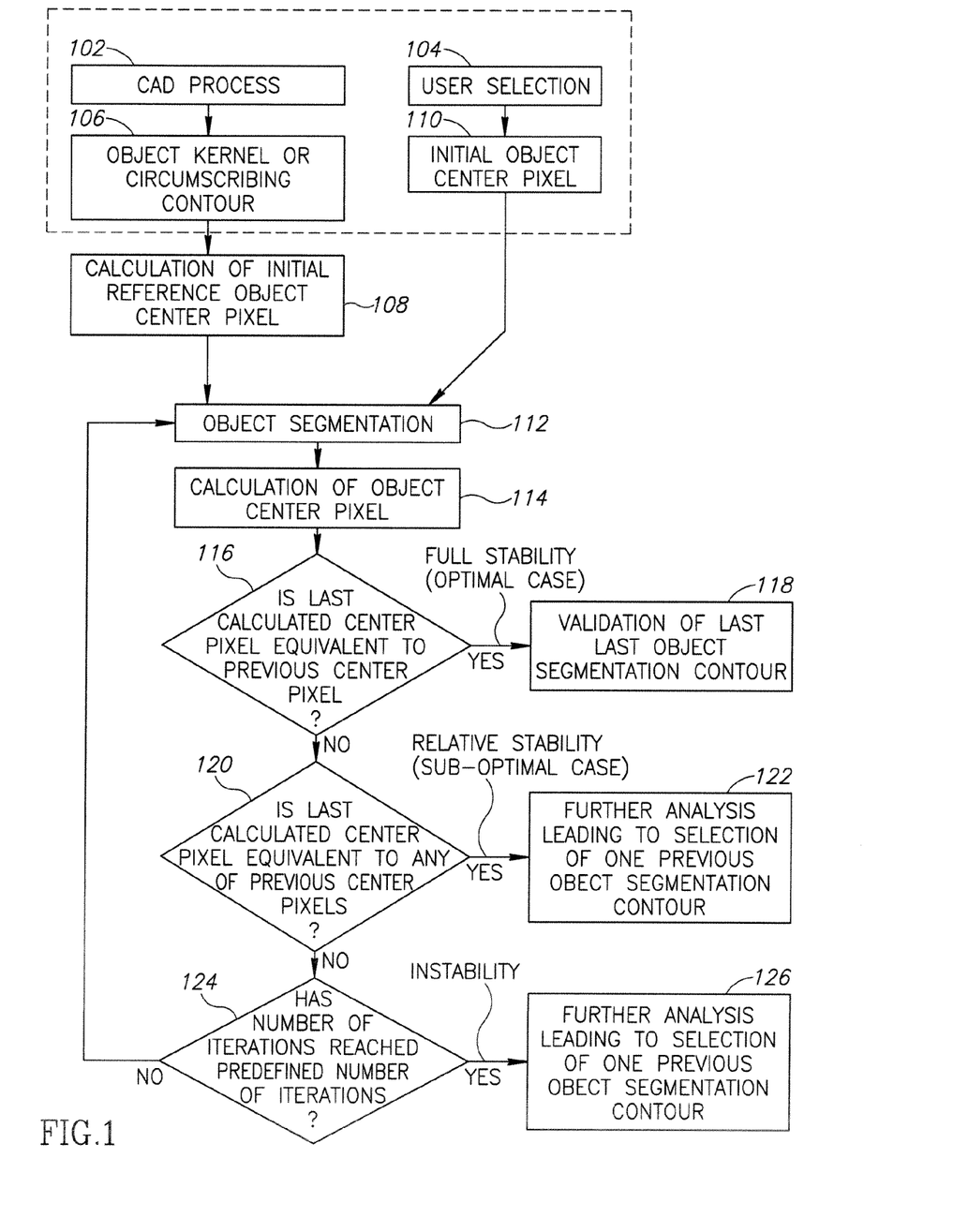
FIG. 1 shows a flowchart of the method of the present invention for segmentation of a mass candidate using iterative determination of an object center.

Reference is now made to FIG. 1 where a flow chart illustrating the method of the present invention is presented.

The method requires first selecting a seed pixel, also referred to here as an initial object center pixel. This seed pixel may be arrived at in one of two ways; the pixel may be user selected or selected by a computer aided diagnosis (CAD) system. In the former case, the user, using a mouse, touch screen, trackball or other input device, selects 104 a pixel deemed to be the initial object center pixel 110. In the latter case, the CAD system 102 may be used to select an object kernel or to provide a circumscribing contour 106 of a mass. The CAD system then calculates 108 an initial object center pixel associated with the contour it has selected.

Regardless of how the seed pixel, i.e. the initial object center pixel, is chosen, the CAD system processor generates an object segmentation 112 by providing a closed segmentation contour within which the selected seed pixel is located.

The new segmentation contour may be calculated using any of many known methods such as region growing or dynamic programming methods. These methods are to be deemed exemplary only. These are not intended to limit usage of other methods that are known to those skilled in the art.

Based on the object segmentation generated in step 112, an object center pixel is calculated 114. The object center pixel may be calculated by any method known to those skilled in the art. These include a. computing the center of gravity of the area enclosed within the segmented contour; b. averaging separately the x and y coordinates of all the pixels located on the segmented contour; and c. computing separately the root mean square of the x and y coordinates of all the pixels located on the segmented contour. These methods are exemplary only and are not to be deemed as limiting. Any other method that can provide an object center pixel within the closed segmentation contour may also be used.

The method of the present invention then includes a comparison and determination 116 of whether the calculated object center pixel and the seed pixel are equivalent. If they are equivalent, the object segmentation is deemed to be valid 118.

The criterion for equivalence may be selected from a group of criteria including the following: a. full coordinate identity of the calculated and reference object center pixels; b. a maximum defined distance between the calculated and reference object center pixels; c. a minimum percentage of the area enclosed by the contour corresponding to the calculated object center pixel overlapping the area enclosed by the contour corresponding to the reference object center pixel. In the first cycle, the reference object center pixel is the seed pixel. It should be readily understood by one skilled in the art that other criteria could be used and the listed criteria are not to be deemed limiting.

If in the first cycle of the method the calculated object center pixel and the seed pixel are compared and determined 116 to be non-equivalent, the processor returns to calculate 112 a new object segmentation using the last calculated object center pixel. A new calculated object center pixel is then calculated 114 based on the new object segmentation and a comparison 116 is made as above between the last calculated object center pixel and the immediate previously calculated object center pixel, the latter functioning as the new reference object center pixel. If they are equivalent, the last object segmentation is deemed to be a valid segmentation 118. Since no significant difference is observed between two consecutive object center pixels, this is considered to be the optimal case where full stability has been reached. The criteria for equivalence may be chosen as discussed above.

If the last calculated object center pixel and the immediate previously calculated object center pixel are not equivalent, a second comparison 120 is made where the last calculated object center pixel is compared to previously calculated center object pixels. If equivalency is found with one of them, a cyclic situation has been reached and full stability will not be attained. However, this cyclic situation is considered as a sub-optimal case having relative stability. If that is the case, further analysis is carried out and selection of one of the previous object segmentations is made 122.

The further analysis in step 122 may be chosen from among the following group of analyses:
a. choosing the previously calculated object center pixel that is closest to the average position of all of the previously calculated object center pixels and selecting the corresponding segmentation contour for the object;
b. calculating the average position of all of the previously calculated object center pixels and determining thereof a segmentation contour for the object;
c. sorting the previously determined segmentation contours for the mass object according to their enclosed surface and selecting the segmentation contour corresponding to the median surface; and
d. calculating the average surface of all of the previously determined segmentation contours for the object and selecting the segmentation contour whose surface is closest to the average surface.

It should be evident to one skilled in the art that the above are only exemplary, non-limiting, choices of analyses: other methods known to those skilled in the art may also be used.

If the second comparison 120 indicates that no equivalence exists between the last calculated object center pixel and any of the previously used object center pixels, a third comparison is made. The processor determines 124 if the number of iterations of steps 112 and 114 and decisions 116 and 120 is less than a predefined number of iterations. If it is less than that predefined number, steps 112 and 114 and decisions 116 and 120 are repeated.

The new object segmentation, i.e. segmentation contour, is calculated 112. The new segmentation contour may be calculated as before using any of many known methods such as:
region growing, and
dynamic programming where one of many possible contours is selected by minimizing a cost function.

These methods are to be deemed exemplary only. These are not intended to limit usage of other methods that are known to those skilled in the art.

If on the other hand, the processor determines 124 that the predefined number of iterations has been reached, the situation is deemed to be unstable and the processor uses further analysis 126 to select one of the previously determined object segmentations.

As discussed above, the further analysis in step 126 may be chosen from among the following group of analyses:
a. choosing the previously calculated object center pixel that is closest to the average position of all of the previously calculated object center pixels and selecting the corresponding segmentation contour for the object;
b. calculating the average position of all of the previously calculated object center pixels and determining thereof a segmentation contour for the object;
c. sorting the previously determined segmentation contours for the mass object according to their enclosed surface and selecting the segmentation contour corresponding to the median surface; and
d. calculating the average surface of the previously determined segmentation contours for the object and selecting the segmentation contour whose surface is closest to the average surface.

It should be evident to one skilled in the art that the above are only exemplary, non-limiting, choices of analyses: other methods known to those skilled in the art may also be used.

Figure 2:
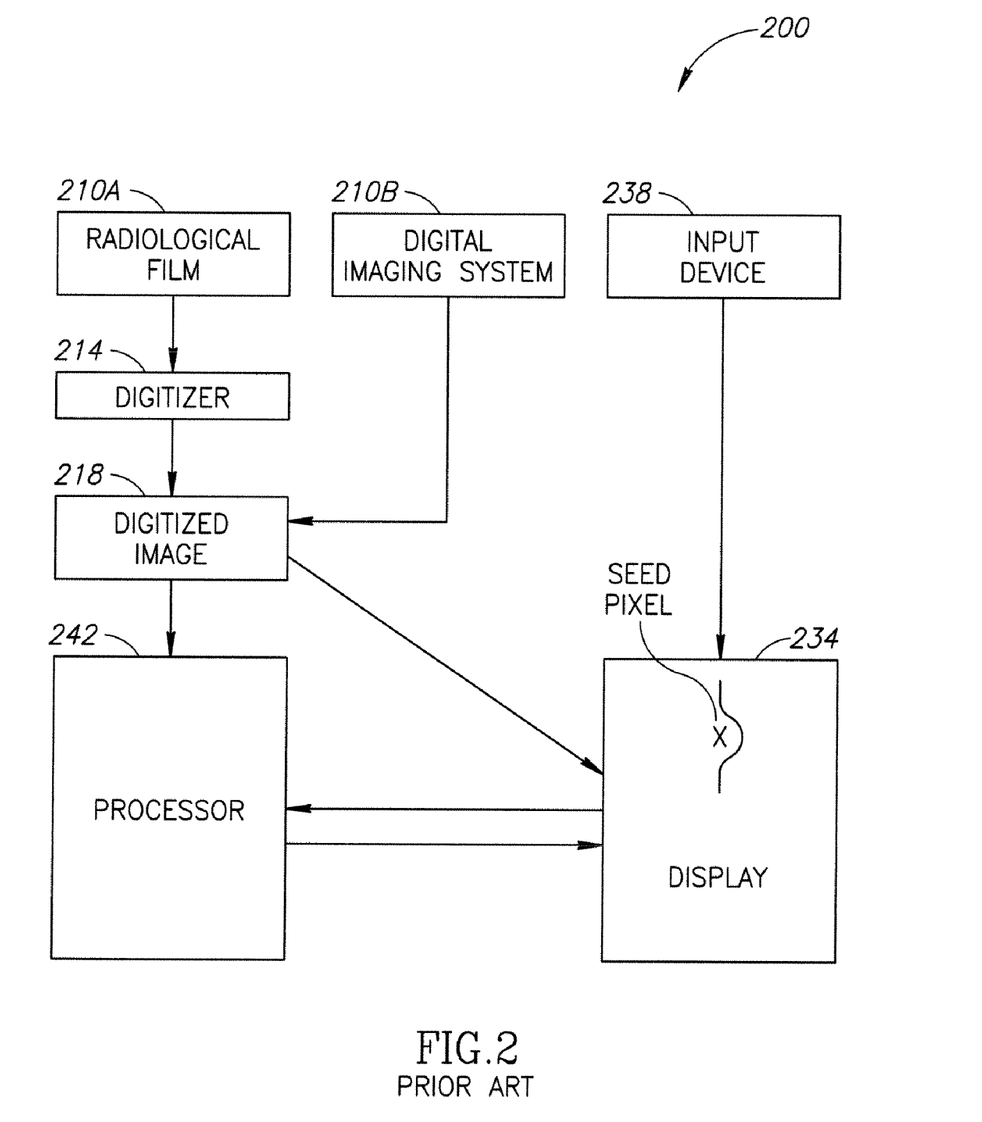
FIG. 2 is a schematic illustration of a prior art system that may employ the method of the present invention.

The above described method may be used with a CAD system such as the prior art system illustrated in FIG. 2 to which reference is now made. The system, generally referenced 200, requires a mammogram provider (210A or 210B) to provide a mammogram. The mammogram provider can be a radiological film system 210A which uses a film mammogram in analog format. A digitizer 214 then converts the film mammogram into a digitized mammogram image 218. Alternatively, the mammogram provider can be a digital imaging system 210B, discussed further below, which provides a digitized image 218 directly. No digitization by digitizer 214 is required when a digitized imaging system 210B is used. Typically, but without being limiting, the film digitizer 214 is a high resolution charged coupled device (CCD) or laser film digitizer. Digitized image 218 is transferred to a display 234 and to a processor 242. It should readily be understood by one skilled in the art that digitized image 218 could also be transferred to display 234 from processor 242 after image 218 is first sent to processor 242.

A digital imaging system 210B used as the mammogram provider may be based on any one of many technologies currently available. These, for example, include, but are not limited to, systems based on magnetic resonance imaging (MRI), computed tomography (CT), scintillation cameras and flat panel digital radiography. All these systems provide radiological mammogram images directly in digital format. If required, the digital mammogram can be reformatted into a digitized mammographic image compatible with processor 242, prior to its being transferred to processor 242.

A user operated input device referenced 238, such as a computer mouse, touch screen, or trackball, is in communication with display 234. The user employing the input device may indicate directly on the digital image appearing on display 234 a selected initial object center pixel. With the aid of the input device, an initial object center pixel, i.e. seed pixel, of the breast is typically circumscribed by a closed curve. Without being limiting, the curve can be circular, polygonal or elliptical. Alternatively, a single point instead of a closed contour may be indicated with the input device (step 110 of FIG. 1). Information may be transferred from display 234 to processor 242 as to the location of the seed pixel selected on the digital image and the object segmentation may then be determined step 112 (FIG. 1). In other instances processor 242 is programmed to determine 108 (FIG. 1) an initial object center pixel, i.e. seed pixel. The seed pixel in FIG. 2 is indicated by an "X".

It should also be understood by one skilled in the art that the predetermined number of iterations noted in comparison step 124 (FIG. 1) may either 1. be inputted by the user or 2. selected by processor 242 of the CAD system according to previously programmed criteria.

Display 234 shows a complete breast with a selected initial object center pixel, i.e. seed pixel, displayed thereon. Display 234 could also, and usually does, provide an expanded view of the digital image being analyzed.

While the segmentation of breast tissue has been discussed above in conjunction with FIGS. 1 and 2, it should be evident to those skilled in the art that the method for segmentation described in FIG. 1 may also be used when segmenting images of tissues other than breast tissue from their image backgrounds. This is true regardless of the modalities used. These modalities may include those discussed herein below. The method can easily be generalized to the segmentation of objects in 3-D modalities. Tissue other than breast tissue that has been, or can be, imaged and segmented using the method described above, include inter alia lung, brain, colon and bone tissue. The method discussed herein above may be applied to these other tissue types, with little or no modification. While the tissue will generally be human tissue, the method may be used on other mammalian tissue as well.

While the current invention may be based on the use of analogue film mammograms which an image digitizer converts to a digital image, it should be remembered that as indicated in FIG. 2 a direct digital imaging system 210B can be used instead. Digital imaging system 210B will then function as a mammogram provider and may be based on any one of many technologies currently available. These, for example, include, but are not limited to, modalities based on magnetic resonance imaging (MRI), ultrasound (US), computed tomography (CT), scintillation cameras, flat panel digital radiography (DR) and computerized radiography (CR). All these modalities provide breast images directly in digital format. The method and system discussed above can be applied to all such modalities with little modification.

Table I below shows other modalities, tissues, and pathologies to which the methods and systems of the present invention may be applied.

It should be readily understood by one skilled in the art that the iterative method described herein may be used to segment objects in all types of digital images. These images do not necessarily have to be images of biological tissue.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

It will be appreciated by persons skilled in the art that the present invention is not limited by the Figure and description hereinabove presented. Rather, the invention is defined solely by the claims that follow.

TABLE I

Use of Different Modalities on Different Tissue Systems for Different Pathologies

| Lesion | Modality | Pathology |
| --- | --- | --- |
| Lung nodules | CT, Conventional radiography | Malignancy |
| Lung Tuberculosis | Conventional radiography | Tuberculosis |
| Intestinal tumors/polyps | CT, Virtual colonoscopy | Malignancy |
| Coronary artery calcified plaque | CT/multislice or electron beam | Infarct |
| Breast tumors | Ultrasound, Magnetic resonance imaging (MRI) | Malignancy |
| Bone tumors | CT, Conventional radiography | Pathological fractures |

The invention claimed is:

1. A method for segmenting an object appearing in a digital image said method comprising the following steps:

selecting a seed pixel of the object;

separating the object from its background in the digital image by determining a segmentation contour around the seed pixel;

calculating a centermost pixel within the segmentation contour;

comparing the calculated centermost pixel to the seed pixel, and if they are deemed equivalent according to a predefined criterion, accepting the segmentation contour from which the calculated centermost pixel was determined; and when the calculated centermost pixel and the seed pixel are deemed to be non-equivalent, then segmentation of the object is repeated using the calculated centermost pixel as a new seed pixel;

wherein the calculated centermost pixel is compared to one or more previously calculated centermost pixels and the repeating of the segmentation of the object using the calculated centermost pixel is only performed when the calculated centermost pixel is determined to be non-equivalent to any of the one or more previously calculated centermost pixels.

2. The method of claim 1, wherein when the calculated centermost pixel is determined to be equivalent to one of the one or more previously calculated centermost pixel, one of the following steps is performed:

choosing a previously calculated centermost pixel of the one or more previously calculated centermost pixels that is closest to an average position of the previously calculated centermost pixels and selecting a corresponding segmentation contour for the object;

calculating the average position of the previously calculated centermost pixels and determining thereof a segmentation contour for the object;

sorting the previously determined segmentation contours for the object according to their enclosed surface and selecting the segmentation contour corresponding to the median surface; and calculating the average surface of the previously determined segmentation contours for the object and selecting the segmentation contour whose surface is closest to the average surface.

3. The method of claim 1, wherein after segmentation of the object is repeated using the calculated centermost pixel as a new seed point, a new segmentation contour is determined and a new centermost pixel calculated, then the new centermost pixel is compared to the previous centermost pixel, and when the new centermost pixel is determined to be equivalent to the previous centermost pixel, the new segmentation contour is used for the object.

4. The method of claim 1, wherein the segmentation of the object is repeated using the calculated centermost pixel as a new seed pixel until either equivalence between a previous calculated centermost pixel and a new centermost pixel is found or until a maximum number of repetitions have been performed.

5. The method of claim 1, wherein the criterion for equivalence is selected from a group consisting of the following criteria:

full spatial coordinate identity of the calculated centermost pixel and the seed pixel;

a maximum defined distance between the calculated centermost pixel and the seed pixel; and a minimum percentage of the area enclosed by the contour corresponding to the calculated centermost pixel overlapping the area enclosed by the contour corresponding to the reference seed pixel.

6. The method of claim 1, wherein the segmentation contour is determined by region growing or dynamic programming in which one of many possible contours is selected by minimizing a cost function.

7. The method of claim 1, wherein calculating the centermost pixel includes computing the center of gravity of the area enclosed within the segmented contour.

8. A method for segmentation of a mass object appearing in a digital image of mammalian tissue, the digital image provided by a medical image acquisition system and the method used with a computer aided diagnosis (CAD) system, said method comprising the following steps:

choosing a seed pixel of the mass object in the digital image;

separating the mass object from its background by determining an initial segmentation contour for the object around the seed pixel;

calculating centermost pixel within the segmentation contour;

comparing the calculated centermost pixel to the seed pixel;

accepting the segmentation contour if the calculated centermost pixel is deemed equivalent to the seed pixel in said step of comparing;

if the calculated centermost pixel is not deemed to be equivalent to the seed pixel in said step of comparing, executing a second step of comparing where the last calculated centermost pixel is compared to previously calculated centermost pixels; and where if the last calculated centermost pixel is deemed equivalent to a previously calculated centermost pixel in said second step of comparing, said method includes a step of further analysis, whereby one of the previously determined segmentation contours is accepted; and where if the last calculated centermost pixel is not deemed equivalent to a previously calculated centermost pixel in said second step of comparing, repeating said steps of choosing, separating, comparing, accepting and said second step of comparing, and wherein the seed pixel in the initial cycle of said method is a user or CAD system selected pixel, and in all said steps of repeating of said method it is the immediate previously calculated centermost pixel.

9. A method according to claim 8, wherein the analysis in said step of further analysis is selected from a group consisting of the following types of analysis:

a. choosing the previously calculated centermost pixel that is closest to the average position of the previously calculated centermost pixels and selecting the corresponding segmentation contour for the object;

b. calculating the average position of the previously calculated centermost pixels and determining thereof a segmentation contour for the object;

c. sorting the previously determined segmentation contours for the mass object according to their enclosed surface and selecting the segmentation contour corresponding to the median surface; and d. calculating the average surface of the previously determined segmentation contours for the object and selecting the segmentation contour whose surface is closest to the average surface.

10. A method according to claim 8, wherein said step of repeating is performed when the number of previous iteration cycles is less than a predefined number of iteration cycles.

11. A method according to claim 10, wherein when the number of segmenting iterations is equal to a predefined number of iteration cycles, said method includes a step of further analysis whereby one of the previously determined segmentation contours is accepted.

12. A method according to claim 11, wherein the analysis in said step of further analysis is selected from a group consisting of the following types of analysis:

a. choosing the previously calculated centermost pixel that is closest to the average position of the previously calculated centermost pixels and selecting the corresponding segmentation contour for the object;

b. calculating the average position of the previously calculated centermost pixels and determining thereof a segmentation contour for the object;

c. sorting the previously determined segmentation contours for the mass object according to their enclosed surface and selecting the segmentation contour corresponding to the median surface; and d. calculating the average surface of the previously determined segmentation contours for the object and selecting the segmentation contour whose surface is closest to the average surface.

13. A method according to claim 8, wherein the criterion for equivalence is selected from a group consisting of the following criteria:

a. full spatial coordinate identity of the calculated centermost pixel and the selected seed pixel;

b. a maximum defined distance between the calculated centermost pixel and the selected seed pixel; and c. a minimum percentage of the area enclosed by the contour corresponding to the calculated centermost pixel overlapping the area enclosed by the contour corresponding to the seed pixel.

14. A method according to claim 8, wherein said step of separating, calculating the centermost pixel within the segmented mass object is effected by computing the center of gravity of the area enclosed within the segmented contour.

15. A method according to claim 8, wherein the segmentation contour in said step of separating is effected using a method selected from a group consisting of the following methods:
region growing and dynamic programming where one of many possible contours is selected by minimizing a cost function.

16. A method for segmentation of an object appearing in a digital image, said method comprising:
providing a seed pixel;
separating the object from its background in the digital image by determining a segmentation contour for the object around the seed pixel;
calculating a centermost pixel within the segmentation contour;
comparing the calculated centermost pixel to the seed pixel, and if they are deemed equivalent according to a predefined criterion, accepting the segmentation contour from which the calculated centermost pixel was determined; and
if the calculated centermost pixel and the seed pixel are deemed to be non-equivalent, iterating said steps of providing, separating and comparing until equivalence is reached or until a predefined number of iterations is reached, whichever is first,
wherein the seed pixel in the initial cycle of said method is a user or CAD system selected pixel, and in all said steps of iterating, the seed pixel is the immediate previously calculated centermost pixel.

17. A method according to claim 16 further including, prior to said step of iterating, a second step of comparing wherein the seed pixel is compared to previously calculated centermost pixels and if no equivalence is found effecting said step of iterating, and if equivalence is found, said method further includes a step of applying other analysis to select one of the previously determined segmentation contours.

18. A method according to claim 17, wherein the analysis in said step of applying other analysis is selected from a group consisting of the following types of analyses:
a. choosing the previously calculated centermost pixel that is closest to the average position of the previously calculated centermost pixels and selecting the corresponding segmentation contour for the object;
b. calculating the average position of the previously calculated centermost pixels and determining thereof a segmentation contour for the object;
c. sorting the previously determined segmentation contours for the object according to their enclosed surface and selecting the segmentation contour corresponding to the median surface; and
d. calculating the average surface of the previously determined segmentation contours for the object and selecting the segmentation contour whose surface is closest to the average surface.

19. A method according to claim 16, wherein if equivalence is not reached before the predefined number of iterations is reached, said method further includes a step of applying other analysis selected from a group consisting of the following types of analyses:
a. choosing the previously calculated object center pixel that is closest to the average position of the previously calculated object center pixels and selecting the corresponding segmentation contour for the object;
b. calculating the average position of the previously calculated object center pixels and determining thereof a segmentation contour for the object;
c. sorting the previously determined segmentation contours for the object according to their enclosed surface and selecting the segmentation contour corresponding to the median surface; and
d. calculating the average surface of the previously determined segmentation contours for the object and selecting the segmentation contour whose surface is closest to the average surface.

20. The method of claim 1, wherein calculating the centermost pixel includes
averaging separately the x and y coordinates of all the pixels located on the segmented contour.

21. The method of claim 1, wherein calculating the centermost pixel includes computing separately the root mean square of the x and y coordinates of all the pixels located on the segmented contour.

22. A method according to claim 8, wherein said step of separating, calculating the object centermost pixel within the segmented mass object is effected by averaging separately the x and y coordinates of all the pixels located on the segmented contour.

23. A method according to claim 8, wherein said step of separating, calculating the object centermost pixel within the segmented mass object is effected by computing separately the root mean square of the x and y coordinates of all the pixels located on the segmented contour.

* * * * *